United States Patent [19]  [11] 3,977,836
Matsuda et al.  [45] Aug. 31, 1976

[54] METHOD AND APPARATUS FOR DETERMINING AMMONIA CONCENTRATION OF GAS

[75] Inventors: Shimpei Matsuda; Fumito Nakajima, both of Hitachi; Masato Takeuchi, Katsuta; Shigeo Uno; Akira Kato, both of Hitachi; Makoto Imanari; Yoshihisa Watanabe, both of Ibaraki, all of Japan

[73] Assignees: Hitachi, Ltd.; Mitsubishi Petrochemical Company Limited; Babcock-Hitachi K.K., all of Japan

[22] Filed: Nov. 12, 1975

[21] Appl. No.: 631,198

[30] Foreign Application Priority Data
Nov. 13, 1974  Japan............................ 49-129943

[52] U.S. Cl. .......................... 23/232 R; 23/232 E; 23/254 R; 23/254 E
[51] Int. Cl.² ................. G01N 25/22; G01N 21/58; G01N 21/12
[58] Field of Search .......... 23/232 R, 232 E, 254 R, 23/254 E, 255 R, 255 E; 73/23

[56] References Cited
UNITED STATES PATENTS

| 3,647,387 | 3/1972 | Benson et al. | 23/232 R |
| 3,870,468 | 3/1975 | Neti | 23/232 R |
| 3,877,875 | 4/1975 | Jones et al. | 23/232 X |
| 3,904,371 | 9/1975 | Neti et al. | 23/232 R |

Primary Examiner—R.E. Serwin
Attorney, Agent, or Firm—Craig & Antonelli

[57] ABSTRACT

An ammonia gas to be determined, and an oxidative gas containing nitrogen oxides in moles more than those of the ammonia are brought into contact with an analytical catalyst capable of forming nitrogen and water from ammonia and nitrogen oxides.

Concentrations of nitrogen oxides of the gas before and after the contact with the analytical catalyst are determined, and an ammonia concentration of the gas is determined by converting the difference between the concentrations of nitrogen oxides to the ammonia concentration by calculation.

13 Claims, 8 Drawing Figures

METHOD AND APPARATUS FOR DETERMINING AMMONIA CONCENTRATION OF GAS

BACKGROUND OF THE INVENTION

This invention relates to a method and apparatus for simply and rapidly determining an ammonia concentration of a gas by reacting nitrogen oxides with ammonia, and obtaining the ammonia concentration from a change in concentrations of the nitrogen oxides.

Heretofore, (1) neutralization-titration method, (2) indophenol method, (3) Nessler method, (4) solution electro-conductivity method, (5) infrared absorption method, and (6) detector tube method have been available as analytical methods for ammonia, as set forth in Japanese Industrial Standards. However, the neutralization-titration method (1) has such disadvantages that the method is influenced with a presence of basic and acidic gas components together with ammonia, and the method is not appropriate for a low ammonia concentration range, for example, less than 100 ppm.

The indophenol method (2) and the Nessler method (3) have a high analytical precision, but require at least one hour for conducting an absorption operation and color-developing operation, and therefore fail to meet a requirement for rapid and continuous analysis.

The solution electro-conductivity method (4) needs various complicated pretreatments, if a sample contains sulfuric acid, halogens, etc. which can change the electro-conductivity, and therefore lacks in rapidity.

The infrared absorption method (5) has a low detection sensitivity, and therefore is not suitable for the analysis in a low concentration range. The detector tube method (6) can only teach the concentration of a sample in a rough value.

On the other hand, analysis of ammonia in the atmosphere or other industrial flue gases requires an accurate and rapid determination in a relatively low concentration range and in the presence of various coexisting gas components, and also requires a continuous automatic analysis. Therefore, the analytical methods for ammonia, as mentioned above, cannot satisfy these requirements. Especially important is an analytical method for ammonia in apparatuses for removing nitrogen oxides in boiler flue gas or gases evolving from the nitric acid industry by reducing nitrogen oxides with ammonia. In such apparatuses, a flue gas containing nitrogen oxides (which will be hereinafter referred to as $NO_x$) is admixed with an ammonia gas, and brought into contact with a catalyst at an elevated temperature to reduce $NO_x$ to nitrogen.

If an insufficient amount of the ammonia gas is added thereto, $NO_x$ cannot be completely reduced.

On the other hand, if an excessive amount of the ammonia gas is added thereto, the ammonia gas will leave the $NO_x$ removal plant as an effluent, possibly causing a secondary air pollution. The excessive amount of the ammonia gas also reacts with other components of the flue gas to form various ammonium salts, which have a possibility to clog the piping system or heat exchanger, or the like in the $NO_x$ removal facility. Therefore, accurate, rapid, and continuous quantitative analysis of ammonia and control of the amount of ammonia to be added are required.

Heretofore, the amount of ammonia to be added is determined by measuring the flow rate of a flue gas, and concentration of $NO_x$ or ammonia.

Suppose that:

$C_{NO}$: Concentration of $NO_x$ in flue gas (ppm)
$F$ : Flow rate of flue gas (Nm$^3$/hr.)
$\alpha$ : Moles of ammonia reacting with one mole of $NO_x$ an amount $D$, a feed rate of ammonia necessary for reducing $NO_x$ in the flue gas, is given by the following formula:

$$D = (C_{NO} \times F \times 17 \times 10^{-6} \times \alpha) \div 22.4 \text{ (kg/hr.)}$$

Among the items to be measured, the concentration of $NO_x$ in the flue gas can be measured by analytical methods, such as chemi-luminescence method, constant potential electrolytical method, etc. The flow rate of the flue gas can be measured by calculation on the basis of boiler loads, or by measuring a gas flow rate by means of a pitot tube, orifice, etc., but the calculated or measured values are generally not so accurate. The value $\alpha$ is obtained from said value of $NO_x$ and an alalytical value of ammonia by light absorption method, etc., but it is difficult to carry out accurate and continuous analysis of ammonia. Even if the amount of the reducing agent to be added is exactly calculated, it is not so simple to control the amount of ammonia to be added with a high precision since the amount of $NO_x$ in a flue gas changes with time in the actual plant, or the reaction conditions of the $No_x$ removal plant change. That is, the accurate and continuous determination of the amount of ammonia will make the operation of the $NO_x$ removal facility very convenient.

SUMMARY OF THE INVENTION

An object of the present invention is to provide a novel method for analyzing ammonia.

Another object of the present invention is to provide an analytical method for rapidly and continuously analyzing ammonia even in the presence of various other coexisting gases.

Other object of the present invention is to provide an analytical method of ammonia suitable for an $NO_x$ removal facility for reducing $NO_x$ by ammonia.

Still other object of the present invention is to provide an analytical apparatus for carrying out the analytical methods as described above.

According to the present invention, ammonia and $NO_x$ are brought into contact with a catalyst under specific conditions to form nitrogen and water, where changes in concentration of $NO_x$ are measured and converted to the desired ammonia amounts. The fundamentals of the present invention are based on a finding of such a fact that ammonia and $NO_x$ undergo specific reactions under specific conditions. The reactions are less influenced with other factors, and are very stable. At the same time, the reactions proceed completely in specific forms, and consequently analytical precision is quite enhanced.

Basic reactions used in the present invention are given by the following reaction formulae:

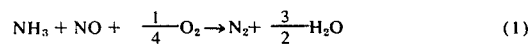   (1)

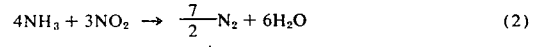   (2)

In the case of $NO \geq NO_2$,

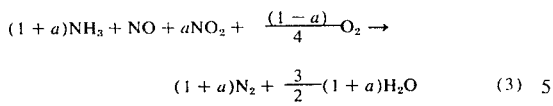

$$(1+a)N_2 + \frac{3}{2}(1+a)H_2O \quad (3)$$

wherein $a \leq 1$.

According to formulae (1) and (3), ammonia reacts with $NO_x$ at a molar ratio of 1 : 1 in an oxidative atmosphere.

In the case that all of $NO_x$ is $NO_2$, the reaction proceeds at a molar ratio of 4 : 3 according to formula (2).

In the case that oxygen is in short in formulae (1) and (3), the following reaction may occur according to formula (4):

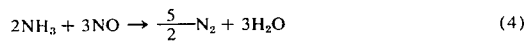

However, it is found from a result of strict measurements that the actual reaction deviates from a molar ratio of 2 : 3 in formula (4), and consequently reaction formula (4) cannot be used for the analysis of ammonia.

It is also said that the reaction of formula (4) occurs even in the presence of oxygen where noble metal catalysts are used, and therefore it is necessary to select the kind of catalysts so that the reaction of formula (4) does not take place.

The catalyst capable of conducting the reactions of said formulae (1), (2) and (3) contains at least one of oxides of vanadium, iron, copper, molybdenum, tin, tungsten and titanium as a component. A sample gas containing ammonia and $NO_x$ is brought into contact with the catalyst at a temperature of 150° to 550°C and a space velocity of 1,000 to 100,000 $hr^{-1}$.

DESCRIPTION OF THE PREFERRED EMBODIMENTS

Figure 1:
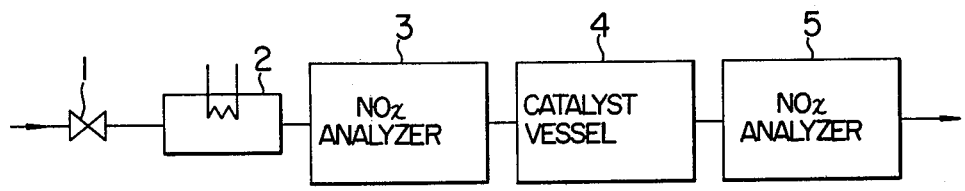
FIGS. 1 to 3 are block diagrams showing main components of the present analytical method, where numeral 1 is a flow rate regulating device, 2 a heater, 3, 5 and 31 $NO_x$ analyzers, 4 a catalyst bed, 21 a flow passage switch means, and 32 an $NO_x$ span gas feeder.

Fundamental of the present method and apparatus for analyzing ammonia is to select reaction conditions under which the said reactions (1), (2) and (3) proceed.

$NO_x$ span gas to react with the ammonia to be measured includes NO and $NO_2$, and the simplest case is the use of No. When there coexist NO and $NO_x$, moles of NO must be made at least equal to or more than the moles of $NO_2$, whereby ammonia and $NO_x$ can undergo reaction at a molar ratio of 1 : 1 strictly (reaction (1) and (3)). In the case of $NO_2$ alone, the reaction proceeds according to the formula (2).

Nitrogen monoxide can be prepared by oxidizing ammonia with a platinum catalyst at an elevated temperature or by reacting copper with nitric acid. The simplest procedure is the use of pressure gas of NO diluted with an inert gas.

When an ammonia concentration of less than several hundred ppm is to be measured, it is preferable to add $NO_x$ so that a concentration of $NO_x$ may be 1.5 to 2 times of the maximum ammonia concentration. When excess $NO_x$ is always in contact with the catalyst for analysis, $NO_x$ is adsorbed on the surface of the catalyst, and therefore the reaction with ammonia immediately starts to take place. If the $NO_x$ concentration becomes lower than the ammonia concentration, it takes several minutes to several tens of minutes in stabilizing the catalyst condition. Therefore, the $NO_x$ concentration in the gas passing through the catalyst bed must be kept always higher.

When a sufficient amount of $NO_x$ is contained in the gas to be measured, the amount of ammonia can be determined directly from a difference in $NO_x$ concentration before and after the passage through the catalyst bed. When an $NO_x$ span gas is to be added to the gas to be measured, gas volume calibration must be made. If the $NO_x$ concentration of the span gas is sufficiently high, the gas volume calibration is negligible, but a slight fluctuation in span gas flow rate can be a cause of great error in the measured value, and therefore the $NO_x$ concentration in the span gas must be specified in accordance to the desired precision of measurement or reliability of instruments.

At least ¼ mole of oxygen, based on ammonia, is necessary for the reaction of ammonia with NO. When the gas to be measured contains no oxygen, oxygen must be added to the gas to be measured or the $NO_x$ span gas. Air can be added in place of oxygen. When the amount of $NO_2$ in the sample gas is greater than that of NO, one oxygen atom of $NO_2$ molecule acts as ½ mole of molecular oxygen (reaction (3)), and consequently, the oxygen addition is not required. That is to say, the reaction of ammonia with $NO_x$ utilized in the present invention is carried out in an oxidative atmosphere with the oxygen gas or nitrogen oxides having more oxygen atoms in one molecule than nitrogen monoxide molecule.

The simultaneous presence of sulfur compounds such as sulfur trioxide and sulfur dioxide, or carbon monoxide, carbon dioxide, or hydrocarbons such as methane gives no adverse effect upon the reaction.

The catalyst capable of accelerating the reaction of ammonia with $NO_x$ to form nitrogen and water contains at least one of oxides of copper, iron, titanium, tin, molybdenum, vanadium and tungsten as an active component. The active component of the catalyst can be supported on a heat-resistant, porous carrier of alumina or titania, or can be in the form of granules of the catalyst components. Readily applicable particle sizes of the catalyst are 50 mesh to several millimeters, and the particle sizes must be selected in view of the presence of dusts in the gas to be measured, form of catalyst vessel, etc.

Temperature of catalyst bed somewhat depends upon the kind of the catalyst, but the desired reaction can be carried out in a temperature range of 200° to 500°C. For example, the reaction can be carried out at 250° to 350°C with a copper catalyst supported on alumina, 250° to 400°C with an iron catalyst supported on alumina, 250° to 450°C with a titanium-molybdenum catalyst, 250° to 500°C with a titanium-tungsten catalyst, and 200° to 450°C with a ternary catalyst of titanium-molybdenum-vanadium. When the reaction temperature is lower than the above-mentioned, the reaction of ammonia with $NO_x$ fails to proceed up to 100 percent, and thus the determined ammonia concentration is lower than the actual one. In the case of higher reaction temperature, oxidation of ammonia by oxygen occurs simultaneously, and consequently the $NO_x$ concentration in the effluent gas is increased, causing the determined ammonia concentration lower than the actual one.

Space velocity of the reaction gas depends upon reaction temperature, and particle sizes and kind of catalyst, but can be between 1,000 and 100,000 $hr^{-1}$.

For the analysis of $NO_x$ in the gas before and after the contact with the catalyst, any analytical procedure, for example, a chemi-luminescence meter, two-wave length light absorption apparatus, infrared analyzer, ultraviolet analyzer, constant potential electrolytical analyzer, etc. can be used, and the analyzer can be selected in view of the $NO_x$ concentration and the desired precision.

Basic structure of the present apparatus for analyzing ammonia is shown in FIG. 1. A gas to be measured, which contains ammonia and a given amount of $NO_x$ is passed through flow rate regulating valve 1 and temperature regulator 2, and an $NO_x$ concentration of the gas before the reaction is measured by $NO_x$ analyzer 3. Then, ammonia and $NO_x$ in the gas undergo reaction in catalyst vessel 4 to form nitrogen and water. Then, an $NO_x$ concentration in the effluent gas after the reaction is measured by $NO_x$ analyzer 5, and an ammonia amount contained in the gas before the reaction can be determined from a difference in $NO_x$ concentrations before and after the reaction.

Figure 2:
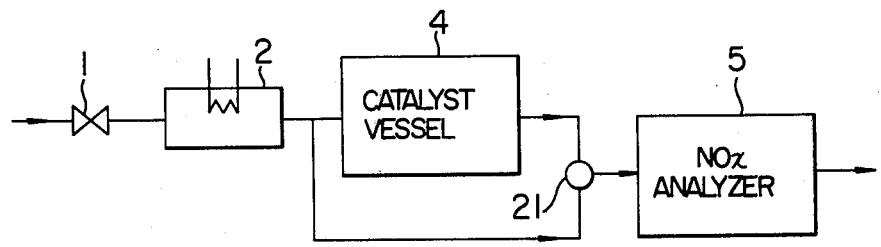

In FIG. 2, a structure of the apparatus using only one $NO_x$ analyzer is shown. The gas is passed through catalyst vessel 4 always at a constant flow rate to maintain a stationary reaction. The gas before and after the reaction is led to $NO_x$ analyzer 5 by means of switch valve 21, and the amount of ammonia can be read directly from the difference in the measured $NO_x$ concentrations.

Figure 3:
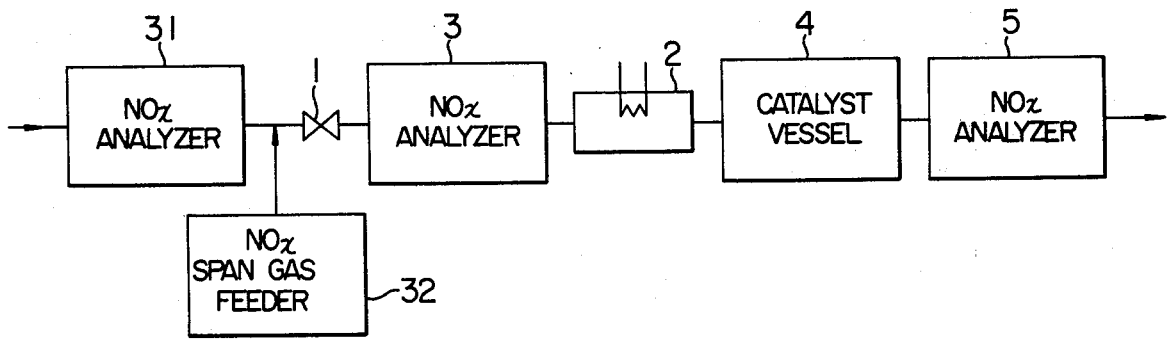

When no $NO_x$ or an insufficient amount of $NO_x$ is contained in the gas to be measured, it is necessary to add an $NO_x$ span gas to the gas. Since the addition of the span gas changes a gas volume, an exact flow rate (ratio of flow rate of the sample gas to that of $NO_x$ span gas) of gas is determined for calibration of the gas volume. The flow rate can be also determined by measuring a coexisting gas component having nothing to do with the reaction, such as carbon dioxide. When the gas to be measured contains a small amount of $NO_x$, an exact amount of ammonia can be determined by calculation of the measured values of $NO_x$, using an apparatus for analysis having a structure of FIG. 3 without measuring the flow rate of the gas. That is, $NO_x$ analyzer 31 for the gas and $NO_x$ span gas feeder 32 added to the basic structure components of FIGS. 1 and 2. $NO_x$ concentration $C_{31}$ of the gas to be measured, $NO_x$ concentration $C_3$ after the span gas addition, $NO_x$ concentration $C_5$ after the reaction, and $NO_x$ concentration $C_{SP}$ of the span gas measured in advance are given thereby. Ammonia concentration $C_{NH_3}$ can be obtained by the following formula:

$$C_{NH_3} = \frac{C_{SP} - C_{31}}{C_{SP} - C_3}(C_3 - C_5)$$

When the $NO_x$ concentration in $NO_x$ span gas is high compared with that in the sample gas ($C_{SP} >> C_{31}$, $C_{SP} >> C_3$), the ammonia concentration in the sample gas is then given by:

$$C_{NH_3} \approx C_3 - C_5.$$

EXAMPLE 1

A sample gas A consisting of 2.5 to 250 ppm of ammonia, nitrogen monoxide at a concentration approximately twice the concentration of ammonia, 3% of oxygen, the balance being a nitrogen gas was prepared.

Figure 4:
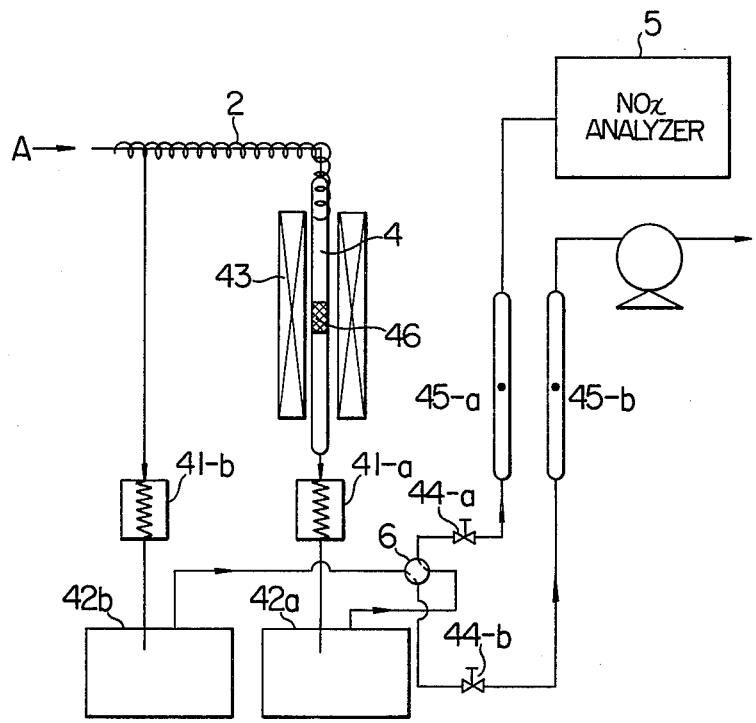
FIG. 4 is a schematic diagram of the present analytical apparatus embodied in Examples, where basically the system of FIG. 2 is modified.

An apparatus for ammonia analysis shown in FIG. 4 was used. The sample gas A was divided into two portions. One portion was heated to a specific temperature by heater 2, and led to catalyst vessel 4. Catalyst vessel 4 was placed in electric furnace 43, and temperature-controlled. The gas passed through the catalyst vessel, and other remaining portion of the sample gas were passed through coolers 41a and 41b, and further through water traps 42a and 42b, respectively, and reached switch valve 6. Then, they were passed through needle-type flow rate-regulating valves 44a and 44b and flow rate meters 45a and 45b, respectively. The one was then led to $NO_x$ analyzer 5, and the other was discharged to the outside. By operation of switch valve 6, the gas passed through catalyst vessel 4 for analysis and the gas not passed therethrough were alternately subjected to measurement of $NO_x$ concentration.

Catalyst vessel 4 for analysis was a stainless steel tube having an inner diameter of 8 mm, and controlled to a catalyst bed temperature 46 of 400°C by tubular electric furnace 43. Catalyst was 10 – 20 mesh granules prepared by compression-molding, calcining and pulverizing a mixture of hydroxides of titanium and tungsten. Reaction was carried out at a space velocity of 10,000 $hr^{-1}$ using 8 ml of the catalyst.

Analysis of $NO_x$ was carried out by an ozone chemi-luminescence method.

Figure 5:
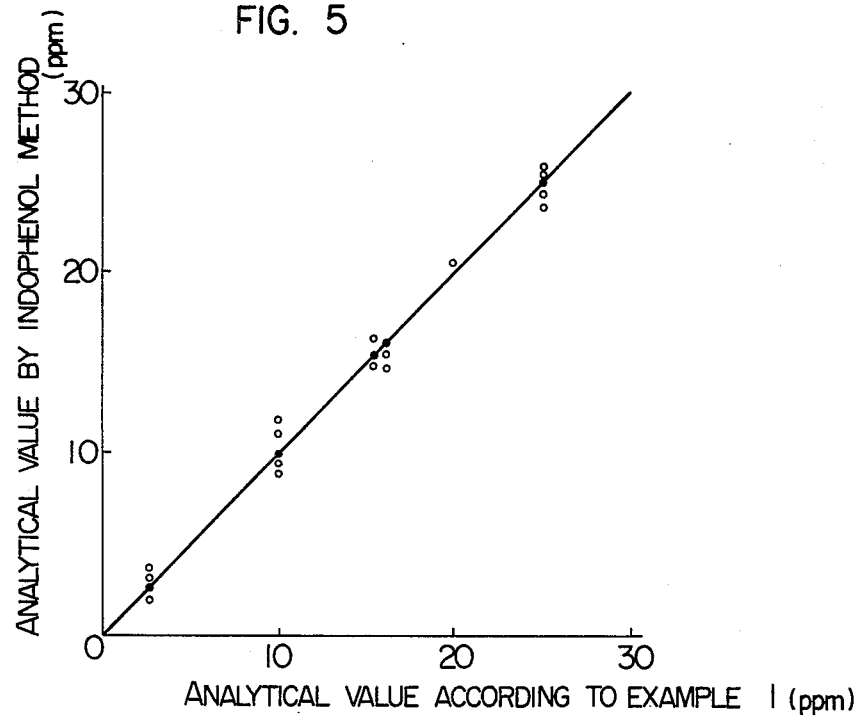
FIGS. 5 and 6 show analytical values of the analytical apparatus of Example 1 calibrated by indophenol method.
Figure 6:
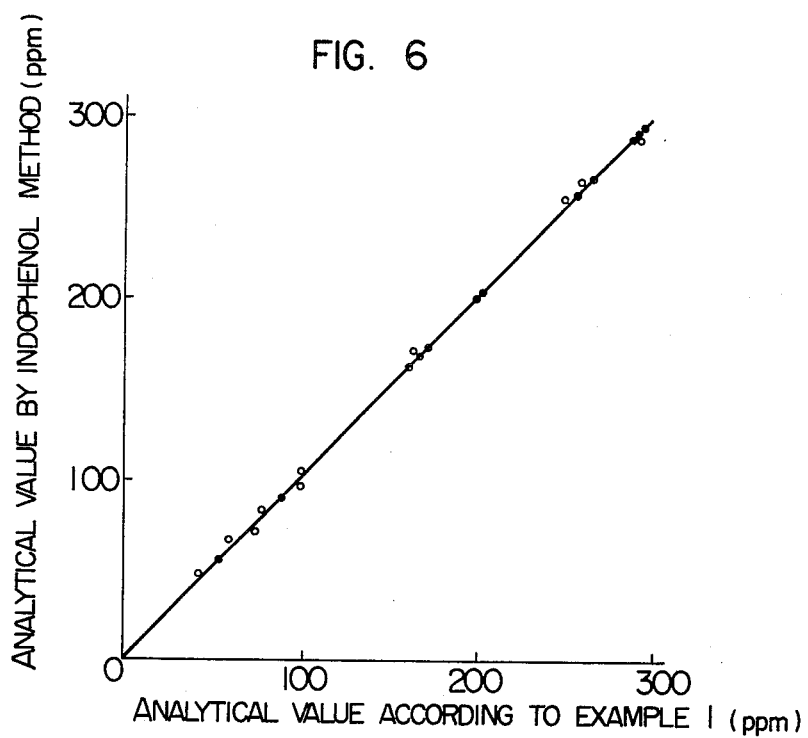

For confirmation of analytical value of ammonia according to the present invention, the amount of ammonia in the gas to be measured was determined by an indophenol method according to Japanese Industrial Standard (JIS). Analytical results obtained according to the present method and the indophenol method are shown in FIGS. 5 and 6.

It was confirmed that in the range of ammonia concentration of 2.5 to 300 ppm (in volume) analytical values of the present analytical method were in good agreement with those of the indophenol method. The analytical values could be read continuously in the present method, whereas it took 1.5 hours for one analysis in the indophenol method.

EXAMPLE 2 ammonia analysis was carried out, using a catalyst which consisted of iron oxide-vanadium oxide supported on alumina at a temperature of 280°C and a space velocity of 8,000 $hr^{-1}$ in the same apparatus for ammonia analysis as in FIG. 4. Composition of the gas to be measured was 0 – 1,000 ppm of ammonia, nitrogen monoxide at a concentration 1.5 times that of ammonia, 500 ppm of sulfur dioxide, 12% of carbon dioxide, 3% of oxygen and 15 percent of steam, the balance being a nitrogen gas.

Analytical results are given in Table 1, together with those obtained by the indophenol method.

Table 1

| Sample No. | 1 | 2 | 3 | 4 | 5 | 6 | 7 |
|---|---|---|---|---|---|---|---|
| Analytical method | (Ammonia concentration, ppm) | | | | | | |
| Analytical values by indophenol method | 0 | 4.3 | 29 | 50 | 113 | 430 | 985 |
| Analytical values by the present invention | 0 | 4.1 | 30 | 52 | 109 | 421 | 991 |

It was found that even in the simultaneous presence of sulfur dioxide and carbon dioxide, the analytical values of the present method were in good agreement with those of the indophenol method.

EXAMPLE 3

An embodiment of applying the present invention to measurement and control of the amount of ammonia to be added in an $NO_x$ removal facility for boiler flue gas is shown.

Figure 7:
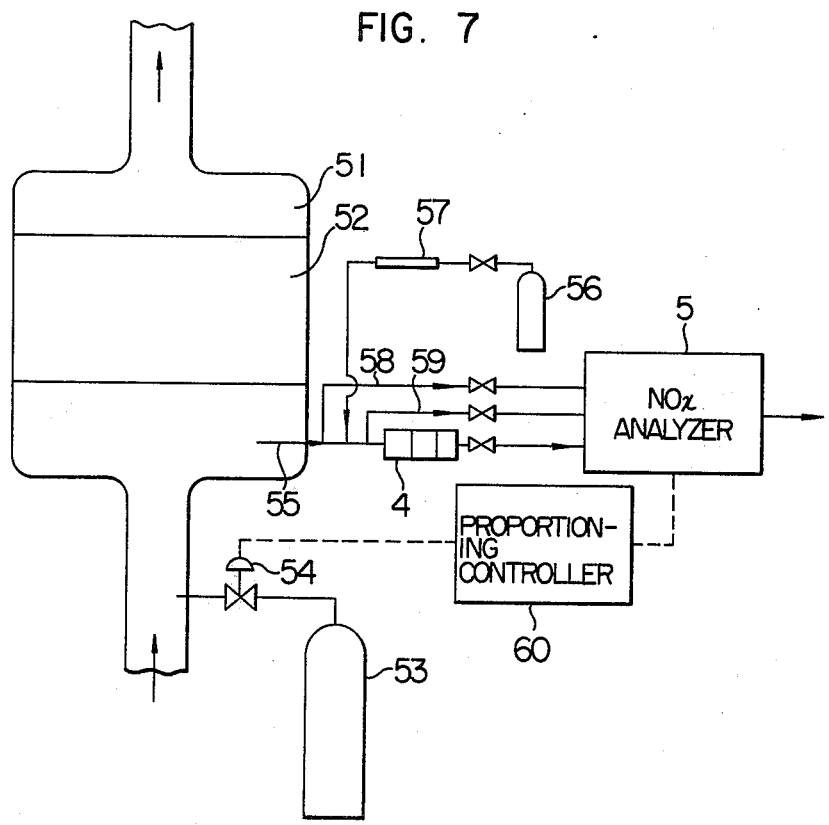
FIG. 7 is a diagram showing main components, where the present analytical apparatus is mounted in a boiler flue gas $NO_x$ removal facility.

In FIG. 7, 1,000 Nm³/hr of a boiler flue gas from combustion of liquefied natural gas as a fuel was passed through $NO_x$ removal reactor 51, where the flue gas is brought in contact with catalyst 52 of Ti-Fe-Mo-V system and $NO_x$ reduction with ammonia takes place. The $NO_x$ reduction with ammonia proceeds at a molar ratio of $NO_x$ to $NH_3$ of 1 : 1, and thus the $NH_3$ concentration at the inlet of the $NO_x$ reduction reactor must be controlled equal to the $NO_x$ concentration. The flow rate of ammonia is regulated by the degree of openning of injection valve 54 of ammonia cylinder 53. The gas to be measured is sampled through gas sampling tube 55 provided at the upstream side of the catalyst bed, and led to $NO_x$ analyzer 5 through piping 58 to measure $NO_x$ concentration $C^1_{NO}$ of the gas. A specific amount of NO span gas is added to the gas to be measured through flow rate meter 57 from NO span gas cylinder 56. $NO_x$ concentration after the addition of NO span gas $C^2_{NO}$ is measured by leading the sample of added gas to $NO_x$ analyzer 5 through piping 59. The gas admixed with the span gas is treated in catalyst vessel 4, and unreacted $NO_x$ concentration $C^3_{NO}$ is measured by $NO_x$ analyzer 5. Ammonia concentration $C_{NH_3}$ is calculated from these $NO_x$ analytical values and $NO_x$ concentration of the span gas $C_{SP}$ measured in advance according to the following formula:

$$C_{NH_3} = \frac{C_{SP} - C^1_{NO}}{C_{SP} - C^2_{NO}}(C^2_{NO} - C^3_{NO})$$

The gas to be measured is sampled at a rate of 3 l/min., and 6 ml of catalyst of Ti-W-V system pulverized to 10 to 20 meshes is filled in catalyst vessel 4. The sampled gas is subjected to reaction for analysis at a space velocity of 20,000 hr⁻¹ and a temperature of 400° ± 5°C. A chemi-luminescence type $NO_x$ analyzer is used as 5, and an automatic control valve 54 for adding ammonia gas is actuated from the resulting analytical values by proportioning control through proportioning controller 60. Continuous operation is carried out for 100 hours by setting $NH_3/NO_x$ of incoming gas to $NO_x$ reduction reactor 51 to 0.85. Analysis according to the present apparatus is carried out at every 2 minutes, and the amount of ammonia to be added is controlled on the basis of the resulting analytical values. To check the controlled state, the ammonia concentration of the incoming gas is measured by the indophenol method and the Nessler method at every 30 minutes at the initial stage of operation, and at every 2 hours after the operation reached a stable state. It is confirmed by determining the ratio of $NH_3/NO_x$ by the chemical analysis, that is, 0.85 ± 0.05 at the initial stage of operation, and 0.85 ± 0.01 after the operation reaches a stable state, that the controlling system embodying the present invention has a sufficient practicality.

To investigate whether the present apparatus can satisfactorily respond to a maximum fluctuation in the flue gas to be treated or not, unsteady states of the present apparatus is observed by increasing the ratio of $NH_3$ to $NO_x$ from 0.85 to 1.10, and then resetting it to 0.90 from 1.10. As a result, it is found that complete stabilization can be obtained within ten minutes after putting a disturbance to the present apparatus, and it is confirmed that the present apparatus can completely satisfy the requirements for the service in the actual plant.

EXAMPLE 4

Figure 8:
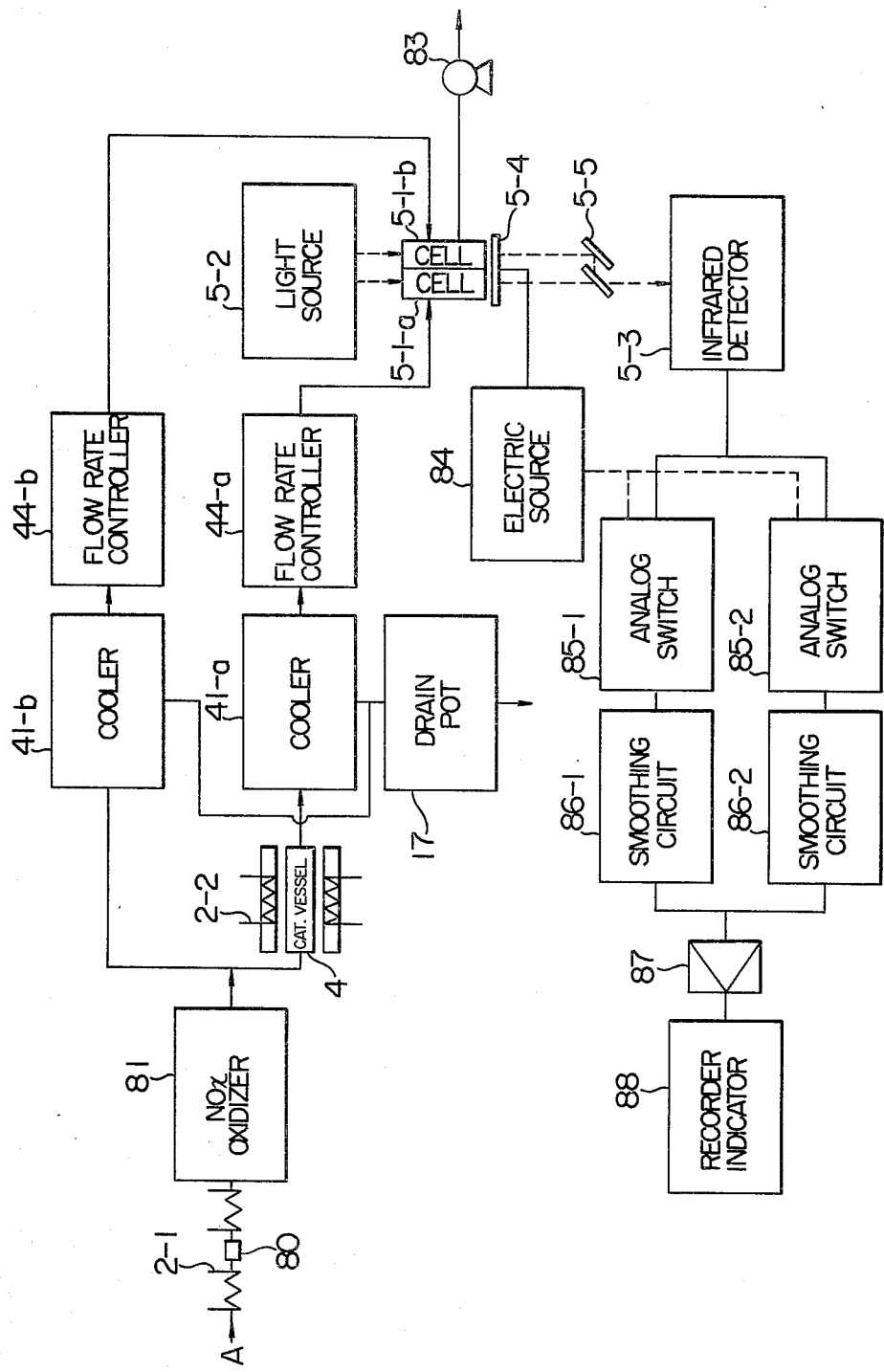
FIG. 8 is a block diagram showing main components where the present invention is made up as a continuous automatic analytical apparatus.

Description is made of an automatic analytical apparatus using an infrared absorption method, referring to FIG. 8.

Sample gas A is passed through a piping kept at an elevated temperature, preferably 300°C or higher, by heaters 2-1, and then filter 80, and reaches No oxidizer (converter) 81. In NO oxidizer 81, NO in sample gas A is converted to $NO_2$, and then the sample gas is divided into two streams. One gas stream is led to catalyst vessel 4 filled with a catalyst and kept to an appropriate temperature by heaters 2-2 to contact the catalyst to complete reaction of ammonia with $NO_2$ in the gas. The effluent gas stream and another gas stream are led through the pipings to coolers 41-a and 41-b, respectively, where the gas streams are cooled, and water contained in the gas streams is removed through drain pot 17. Then, the gas streams are passed through flow rate controllers 44-a and 44-b, and led to cells 5-1-a and 5-1-b, respectively. The gas streams are discharged to the outside through pump 83. While these gas streams pass through cells 5-1-a and 5-1-b, the energy of infrared rays corresponding to $NO_2$ concentrations contained in these gas streams is absorbed from the light entering from light source 5-2. Two light paths of the infrared rays passed through the cells are alternately passed through mirrors 5-5 by chopper 5-4 rotated by electric source 84 for chopper, and reach infrared detector 5-3. By synchronizing a standard signal generated from electric source 84 for chopper with output of the infrared detector, the respective outputs from infrared gas detector 5-3 are distinguised at analog switches 85-1 and 85-2. The respective distinguished outputs are smoothed in smoothing circuits 86-1 and 86-2, and then amplified in operational amplifier 87 to take out an electric output corresponding to the ammonia concentration. The electric output is continuously recorded or indicated on recorder or indicator 88.

According to the present method and apparatus for continuously analyzing ammonia, the ammonia in a sample gas can be continuously analyzed rapidly and accurately without any influence of various coexisting gas components in the sample gas while overcoming the troubles in sampling technique. Such effects of the present invention can be attained especially by the use of catalysts. which we have developed (for example, Ti-Mo, Ti-Mo-V, Ti-Fe, etc.), having an $NO_x$ reduction activity by ammonia. The catalyst is not influenced by the coexisting gas components such as sulfur compounds, for example, $SO_2$ and $SO_3$, carbon dioxide, steam, etc., and has a high activity and a long catalytic life. When a catalyst having an insufficient activity or life or stability is used, the object of the present method and apparatus for continuously analyzing ammonia cannot always be satisfied.

According to the present method and apparatus, ammonia in the sample gas is made to react with $NO_x$ at an elevated temperature, preferably, 300°C or higher, and the target material of direct measurement is $NO_x$. Thus, the sampling technique that is always a problem in the analysis of ammonia is unnecessitated, and the accuracy of the analysis can be remarkably improved.

Another feature of the present method and apparatus for continuously analyzing ammonia is a high sensitivity. That is, since the target material of direct measurement is $NO_x$, an analytical method having a high sensitivity and good stability so far used, for example, a chemi-luminescence method can be used. That is, ammonia can be analyzed with a high sensitivity.

The present method and apparatus for continuously analyzing ammonia can be most effectively applied to the control of the amount of ammonia to be added and suppression of effluent ammonia in a treated flue gas from a catalytic reactor in an $NO_x$ reduction process, the most promising process in the flue gas $NO_x$ removal technology. That is, the ammonia concentration of the sample gas can be rapidly and continuously measured in these applications, and thus countermeasure for rapid control of ammonia flow rate can be taken.

According to the present method and apparatus for continuously analyzing ammonia, $NO_x$ concentration of a sample gas, besides the ammonia concentration, can be determined simultaneously or alone, and thus the present invention can be used as an analyzer for $NH_3$ —NO—$NO_x$.

What is claimed is:

1. A method for determining an ammonia concentration in a gas, which comprises contacting ammonia and nitrogen oxides in moles more than moles of the ammonia with a catalyst capable of promoting reaction of ammonia and nitrogen oxides to form nitrogen and water in an oxidative atmosphere at an elevated temperature, measuring concentrations of nitrogen oxides before and after the contact with the catalyst, and calculating an ammonia concentration from the measured concentrations of nitrogen oxides.

2. A method according to claim 1, wherein the nitrogen oxides are nitrogen monoxide or nitrogen dioxide.

3. A method according to claim 1, wherein the catalyst contains at least one of oxides of titanium, vanadium, iron, copper, molybdenum, tin, and tungsten as active component.

4. A method according to claim 1, wherein the nitrogen oxides is a mixture of nitrogen monoxide and nitrogen dioxide in moles less than moles of nitrogen monoxide.

5. A method for determining an ammonia concentration, which comprises a step of measuring an $NO_x$ concentration ($C_1$) of a gas containing ammonia to be measured; a step of adding an $NO_x$ span gas having a specific concentration ($C_{SP}$) to the gas; a step of measuring an $NO_x$ concentration ($C_2$) of the gas admixed with the span gas; a step of contacting the gas admixed with the span gas with a catalyst capable of promoting reaction of ammonia and nitrogen oxides to form nitrogen and water at a temperature of 200° to 500°C in an oxidative atmosphere; a step of measuring an $NO_x$ concentration ($C_3$) of the gas after the contact with the catalyst; and a step of calculating an ammonia concentration of the gas from said measured $NO_x$ concentrations according to the following formula:

$$\frac{C_{SP} - C_1}{C_{SP} - C_2}(C_2 - C_3).$$

6. A method according to claim 5, wherein the nitrogen oxides are nitrogen monoxide or nitrogen dioxide.

7. A method according to claim 5, wherein the catalyst contains at least one of oxides of titanium, vanadium, iron, copper, molybdenum, tin, and tungsten as an active component.

8. A method according to claim 5, wherein the nitrogen oxides are a mixture of nitrogen monoxide and nitrogen dioxide in moles less than the moles of nitrogen monoxide.

9. A method according to claim 5, wherein the measurement of $NO_x$ concentration is carried out by a chemi-luminescence method.

10. A method according to claim 5, wherein the measurement of $NO_x$ concentration is carried out by an infrared or UV-visible light absorption method.

11. A method for continuously determining an ammonia concentration, which comprises dividing a gas containing ammonia and nitrogen oxides in an amount more than necessary for oxidizing the ammonia into two portions, contacting one portion with a metallic oxide catalyst capable of promoting reaction of ammonia and nitrogen oxides to form nitrogen and water, measuring a concentration of unreacted nitrogen oxides in the one portion and a concentration of nitrogen oxides in another portion continuously, and obtaining an ammonia concentration from a difference in the measured concentrations of nitrogen oxides.

12. An apparatus for determining an ammonia concentration, which comprises an analyzer for measuring and $NO_x$ concentration of a gas containing ammonia to be measured; and $NO_x$ span gas feeder to add $NO_x$ in moles more than moles of the ammonia of the gas to the gas to be measured; an analyzer for measuring an $NO_x$ concentration of the gas admixed with $NO_x$ span gas; a heater for the gas; a catalyst vessel filled with a metallic oxide catalyst capable of promoting reaction of ammonia and $NO_x$ to form nitrogen and water; and an analyzer for measuring an $NO_x$ concentration of the gas leaving the catalyst vessel.

13. An apparatus for continuously determining an ammonia concentration, which comprises a piping for dividing a gas containing ammonia and nitrogen oxides in an amount more than the necessary for oxidizing the ammonia into two streams, a catalyst vessel provided in a piping for the one stream and filled with a catalyst capable of promoting reaction of ammonia and nitrogen oxides to form nitrogen and water; cells for analyzing nitrogen oxides of the two portions of the gas, the gas passing through the respective pipings into the respective cells; a light source irradiating the cells; a light receiving section capable of converting a light energy corresponding to concentrations of nitrogen oxides to an electric energy upon reception of the light from the cells; a filter circuit and/or smoothing circuit, and an operational amplifier for treating the electric energy.

* * * * *